US010881532B1

(12) United States Patent
Cheng et al.

(10) Patent No.: US 10,881,532 B1
(45) Date of Patent: Jan. 5, 2021

(54) SHOCK AND TORSION ABSORBER FOR ELEVATED VACUUM SUSPENSION (71) Applicant: KEN DALL ENTERPRISE CO., LTD., New Taipei (TW)

(72) Inventors: Chia-Pao Cheng, New Taipei (TW); Hsiang-Ming Wu, New Taipei (TW)

(73) Assignee: KEN DALL ENTERPRISE CO., LTD., New Taipei (TW)

( * ) Notice: Subject to any disclaimer, the term of this patent is extended or adjusted under 35 U.S.C. 154(b) by 35 days.

(21) Appl. No.: 16/503,470

(22) Filed: Jul. 4, 2019

(51) Int. Cl.
*A61F 2/50* (2006.01)

(52) U.S. Cl.
CPC ........ *A61F 2/50* (2013.01); *A61F 2002/5003* (2013.01); *A61F 2002/5033* (2013.01); *A61F 2002/5075* (2013.01)

(58) Field of Classification Search
CPC ...... A61F 2/50; A61F 2/26; A61F 2/80; A61F 2002/5003; A61F 2002/5033; A61F 2002/5007; A61F 2002/5006; A61F 2002/802; F16D 33/18
USPC .......................................................... 623/26
See application file for complete search history.

(56) References Cited

U.S. PATENT DOCUMENTS

| 5,702,489 | A | 12/1997 | Slemker | |
|---|---|---|---|---|
| 6,645,253 | B2 | 11/2003 | Caspers | |
| 7,744,653 | B2 | 6/2010 | Rush | |
| 10,406,001 | B2* | 9/2019 | Harris | A61F 2/68 |
| 2003/0191539 | A1* | 10/2003 | Caspers | A61F 2/80 623/35 |
| 2005/0024082 | A1* | 2/2005 | Kitazoe | G09G 3/006 324/760.01 |
| 2009/0036998 | A1 | 2/2009 | Finlinson | |
| 2010/0049332 | A1 | 2/2010 | Selvig | |
| 2015/0276003 | A1* | 10/2015 | Ohta | F16F 9/44 188/317 |
| 2020/0046523 | A1* | 2/2020 | Erdmann | A61F 2/70 |

FOREIGN PATENT DOCUMENTS

| WO | 2005105000 | 11/2005 |
|---|---|---|
| WO | 2016032609 | 3/2016 |

* cited by examiner

*Primary Examiner* — Bruce E Snow
(74) *Attorney, Agent, or Firm* — Leong C. Lei (57) ABSTRACT

The present invention teaches a shock and torsion absorber that includes a base member having an accommodation space and an exhaust opening, a cushion member joined to a bottom end of the base member, a limit member including a positioning element and a seal element, and a joint member having an intake element, a trough, and a axial channel. A piston is housed in the joint member. The axial channel allows a shaft to thread through via the positioning element and to join with the shaft limit element. A bottom end of the positioning element is connected to the cushion member. The piston is connected to a top end of the positioning element. An upper vacuum chamber is formed above the seal element in the joint member. A lower vacuum chamber is formed beneath the piston and the seal element.

6 Claims, 7 Drawing Sheets

SHOCK AND TORSION ABSORBER FOR ELEVATED VACUUM SUSPENSION

BACKGROUND OF THE INVENTION

(a) Technical Field of the Invention

The present invention is generally related to a prosthetic device, and more particular to a shock and torsion absorber for use on a prosthetic limb.

(b) Description of the Prior Art

Shock absorption is commonly found on prosthetic limbs. To offer more comfortable experience to users, manufacturers continue to work on innovative improvements on the design of shock absorption.

For example, U.S. Pat. No. 7,744,653 teaches a vacuum pump having shock absorption and controlled rotation for use in an artificial limb. The pump includes a housing having a first accommodation space, and a shaft configured to be received by and to reciprocate within the first accommodation space. The housing and shaft form a pump accommodation space. A piston is coupled to the shaft and positioned within the pump accommodation space. When the piston is moved upward, air in the pump accommodation space is expelled through an exhaust port. When the piston moves downward, air is drawn from a connected cavity to achieve buffering. A rotational structure involves a pair of blocks within a trough to limit the blocks' moving range. The blocks are made of a flexible material. As a shaft is turned, the blocks are depressed and deformed to allow rotation.

However, even though multiple chambers are provided by the vacuum pump, only one is substantially involved in buffering. As to the rotational structure, the higher number of parts and the way the parts are put together are both complicated, causing difficulty in subsequent maintenance.

On the other hand, U.S. Pat. No. 6,645,253 teaches a vacuum pump and shock absorber where, according to pages 22-25 of the specification, a first chamber 240 is formed in a cylinder 220 above a piston 260, a second chamber 250 is formed above the cylinder 220. A third chamber 241 is formed beneath the piston 260. Initially, the second chamber 250 has the largest capacity, and a first valve device 270 is closed to seal a cavity 62. As a casing 210 moves downward, the second chamber 250 shrinks and air is expelled through a second valve device 280. The air in the third chamber 241 provides shock absorption. As the casing 210 continues to move downward, the first chamber 240 would have the largest capacity and the second chamber 250 would have the smallest capacity. Through this repeated cycle, air flows between chambers to achieve buffering and more comfortable walking experience.

However, the vacuum pump and shock absorber conducts air flow all through an intake/exhaust post 272. Additional complexity is involved so that a single channel is shared for both air intake and exhaust. The number of related chambers also cannot be reduced. Furthermore, as a user walks faster or slower, the fluidity of air flow would be affected, leading to inferior walking experience.

SUMMARY OF THE INVENTION

The present invention teaches a shock and torsion absorber that includes a base member having an accommodation space and an exhaust opening, a cushion member joined to a bottom end of the base member, a limit member including a positioning element and a seal element, and a joint member having an intake element, a trough, and a axial channel. A piston is housed in the joint member. The axial channel allows a shaft to thread through via the positioning element and to join with the shaft limit element so as to buffer the joint member's pressure. An upper vacuum chamber is formed above the seal element in the joint member. A bottom end of the positioning element is connected to the cushion member. The piston is connected to a top end of the positioning element.

When the joint member moves upward, the intake element draws air into the upper vacuum chamber and air in the lower vacuum chamber is expelled through the exhaust opening. When the joint member moves downward, air in the upper vacuum chamber flows to the lower vacuum chamber. Therefore, the joint member may steadily operate in the base member by drawing air alternately by the upper and lower vacuum chambers.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

As shown in FIGS. 1 to 5, a shock and torsion absorber according to an embodiment of the present invention includes a base member 10. The base member has an accommodation space 11 and an exhaust opening 101. A cushion member 12 is joined to a bottom end of the base member 10, and the cushion member 12 includes a casing 121, a shaft limit element 122, an elastic element 123, and an adjustment element 124. The shaft limit element 122 and the elastic element 123 are sequentially received in the casing 121, and a bottom end of the casing 121 is sealed by the adjustment element 124. The elastic element 123 may be a spring, or other element of elastic property. The present invention does not impose specific limitation.

A limit member 20 includes a tubular positioning element 21 and a seal element 22. A bottom end of the positioning element 21 is threaded through the base member 10 and coupled to the cushion member 12. The seal element 22 is joined to a top end of the positioning element 21. A joint member 30 includes an intake element 301 joined to an outer circumference of the joint member 30 to draw air F inside the joint member 30. The joint member 30 has a trough 31 around an inner circumference of the joint member 30, and an axial channel 33. Through the trough 31, a piston 32 is tightly housed in the joint member 30. A shaft 40 runs through the axial channel 33 and the positioning element 21, and joints to the shaft limit element 122 for buffering pressure exerted on the joint member 30. An intake 1-way valve 302 is further configured inside the intake element 301 so that air F is prevented from escaping from the upper vacuum chamber 50 through the intake element 301.

Figure 2:
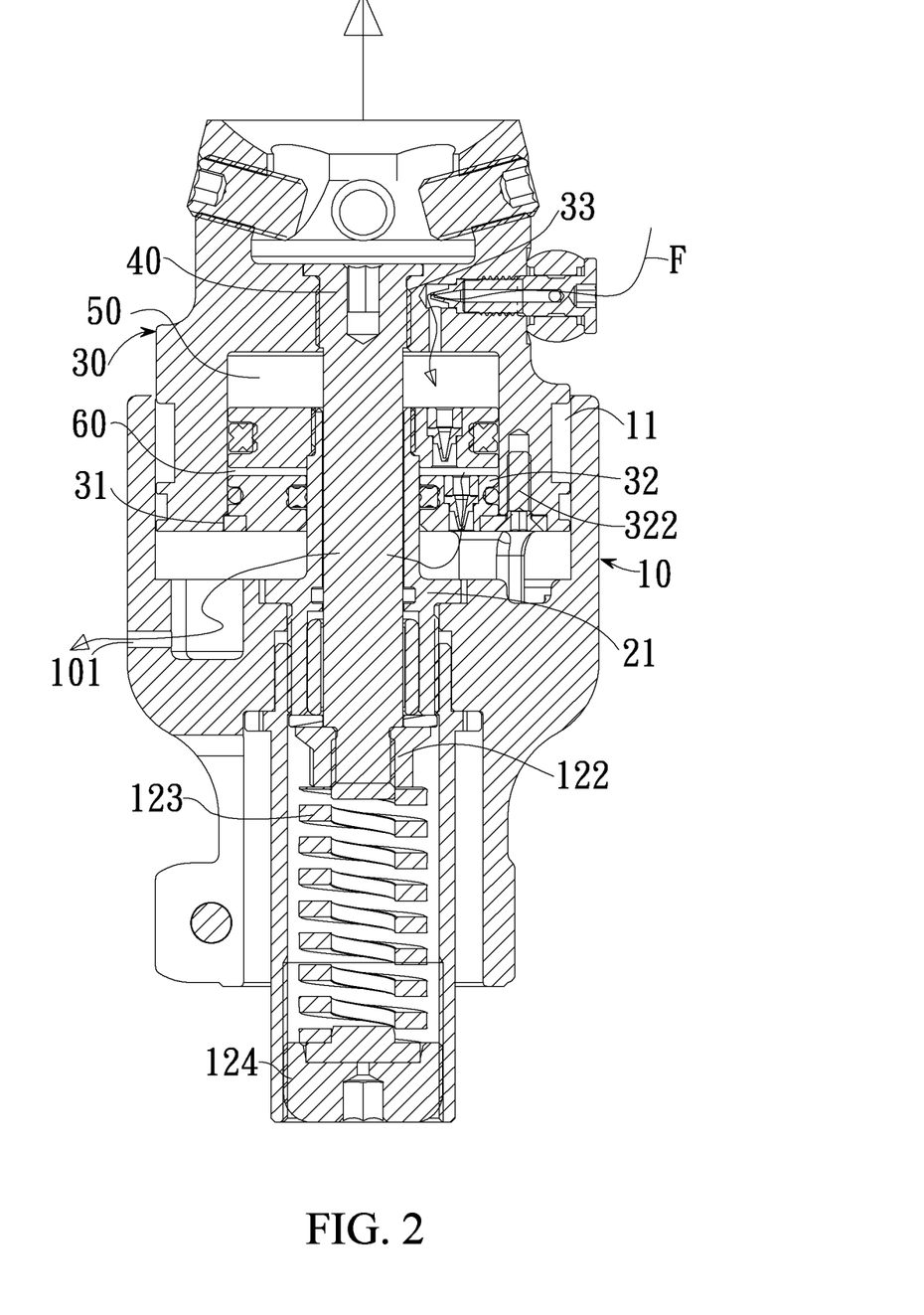
FIG. 2 is a schematic sectional diagram showing a joint member of the shock and torsion absorber of FIG. 1 moving upward.
Figure 3:
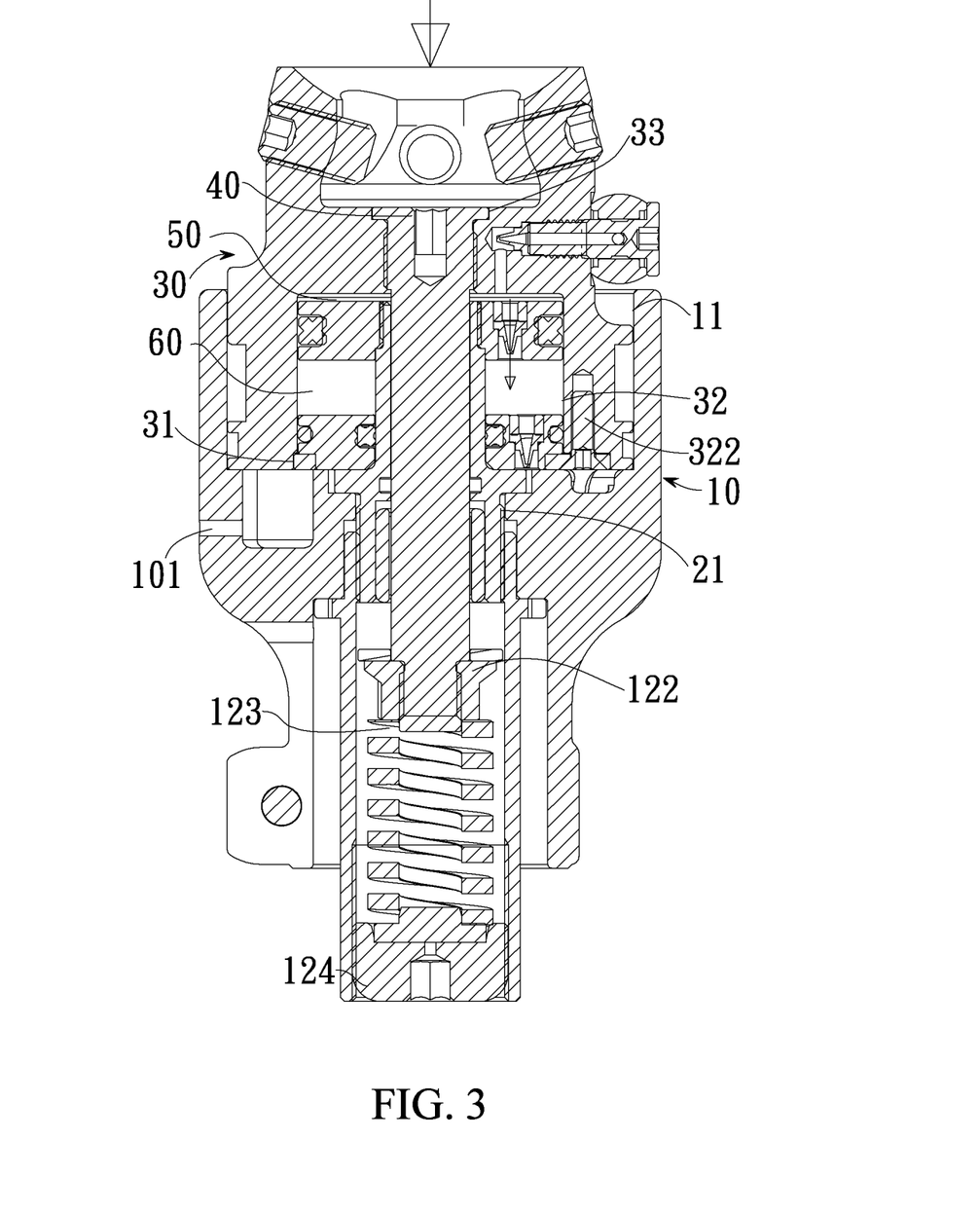
FIG. 3 is a schematic sectional diagram showing a joint member of the shock and torsion absorber of FIG. 1 moving downward.

An upper vacuum chamber 50 is formed inside the joint member 30 above the seal element 22, and a lower vacuum chamber 60 is formed inside the joint member 30 beneath the piston 32 and the seal element 22. When the joint member 30 moves upward, the intake element 301 draws air F into upper vacuum chamber 50 and air in the lower vacuum chamber 60 is expelled through the exhaust opening 101. When the joint member 30 moves downward, air F in the upper vacuum chamber 50 flows to the lower vacuum chamber 60. The joint member 30 therefore operate steadily inside the base member 10.

Figure 1:
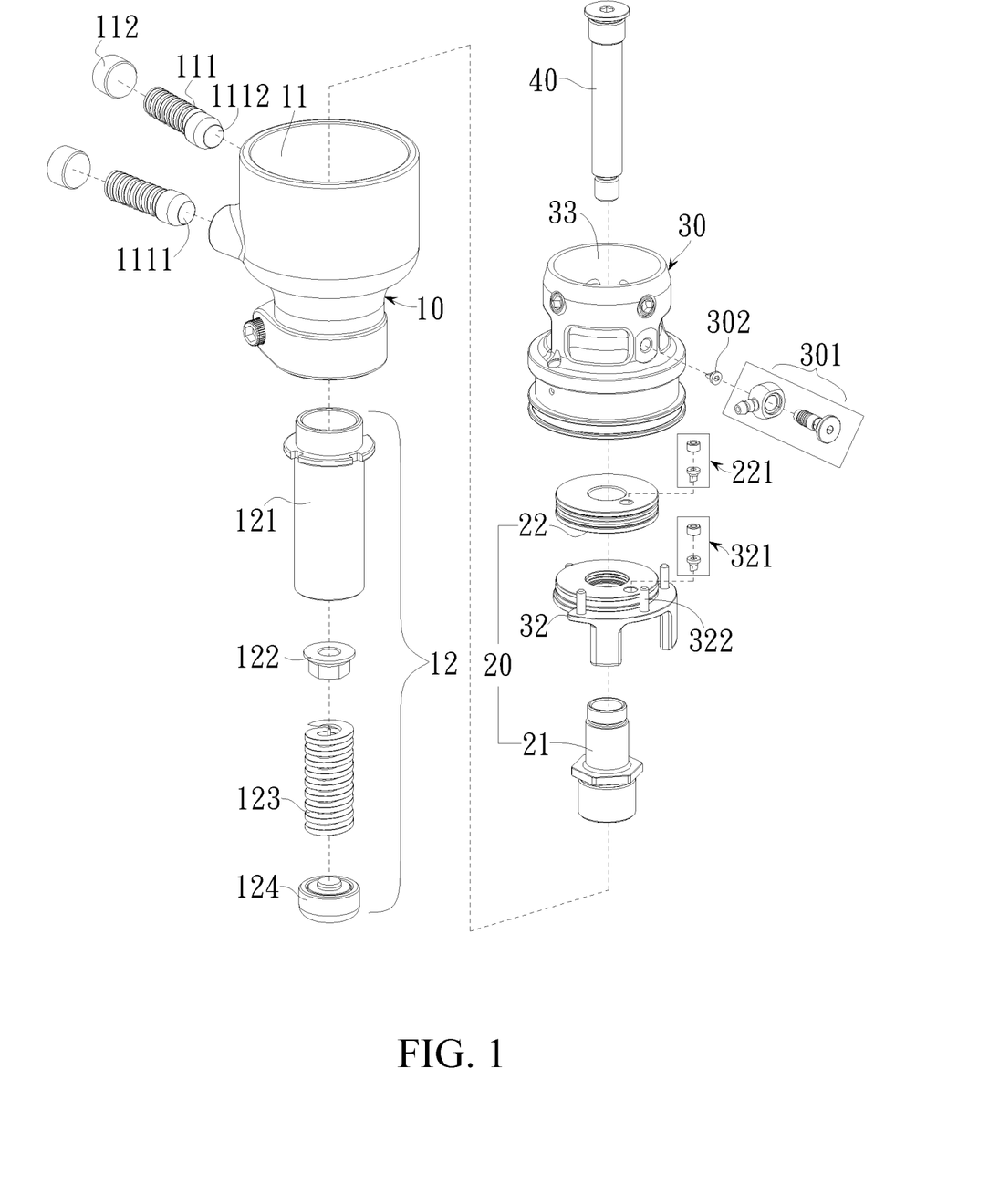
FIG. 1 is a perspective breakdown diagram showing a shock and torsion absorber according to an embodiment of the present invention.
Figure 4:
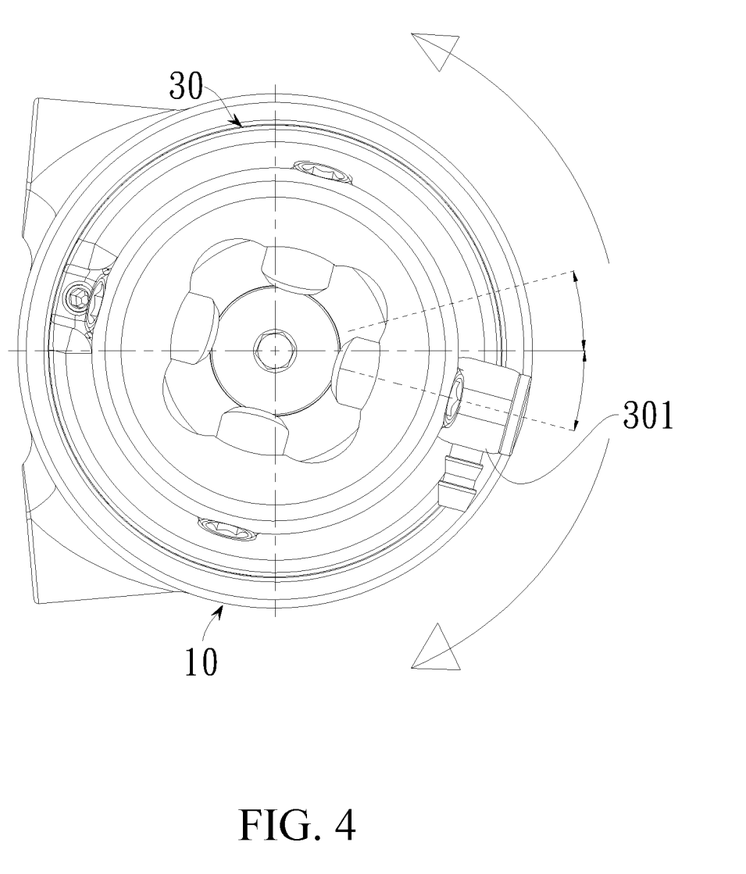
FIG. 4 is a top-view diagram showing the shock and torsion absorber of FIG. 1.
Figure 5:
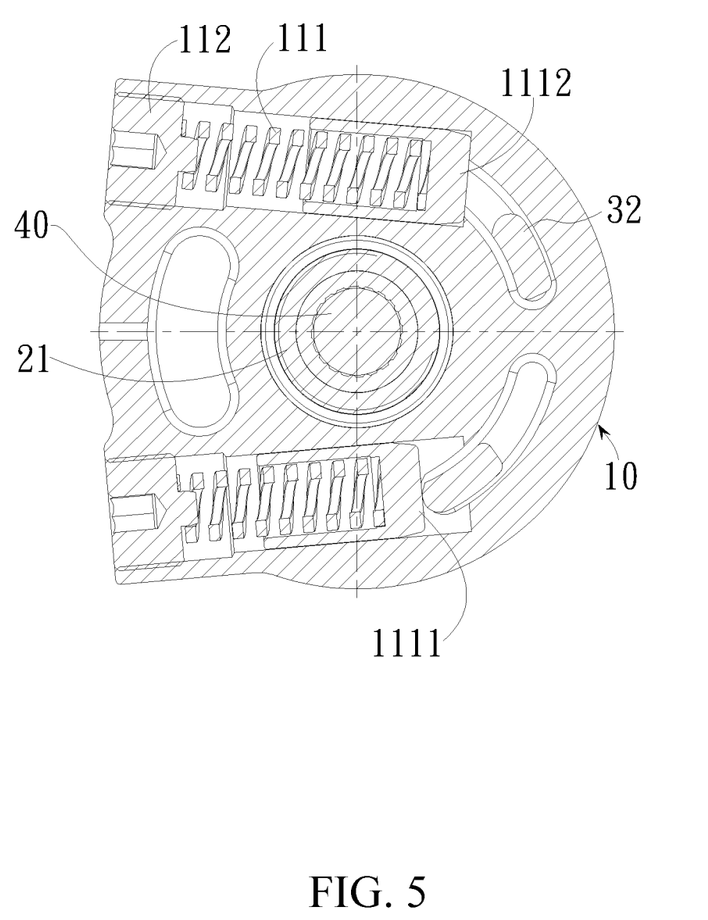
FIG. 5 is a cross-sectional diagram of the shock and torsion absorber of FIG. 4.

Within the accommodation space 11, there are two torsion springs 111 and two strength adjustment screws 112. The torsion springs 111 run through the accommodation space 11. Each torsion spring 111 has a first end 1111 and a second end 1112. A number of pins 322 are extended from a top side of the piston 32. The pins 322 are for fixing the joint member 30 so as to adjust the strength adjustment screws 112's elasticity against the first ends 1111 and second ends 1112, and further to limit the joint member 30's left and right rotational range. In the present embodiment, the joint member 30 has a rotational range that is 15 degrees both clockwise and counterclockwise. This range may be conveniently adjusted according to the elasticity provided by the torsion springs 111.

A seal element 1-way valve 221 is configured in the seal element 22 besides the axial channel so that air F drawn through the intake element 301 into the upper vacuum chamber 50 may enter single-directionally the lower vacuum chamber 60 without backflow. A piston 1-way valve 321 is also configured in the piston 32 besides the axial channel so that air F in the lower vacuum chamber 60 may be expelled single-directionally through the exhaust opening 101.

Figure 6:
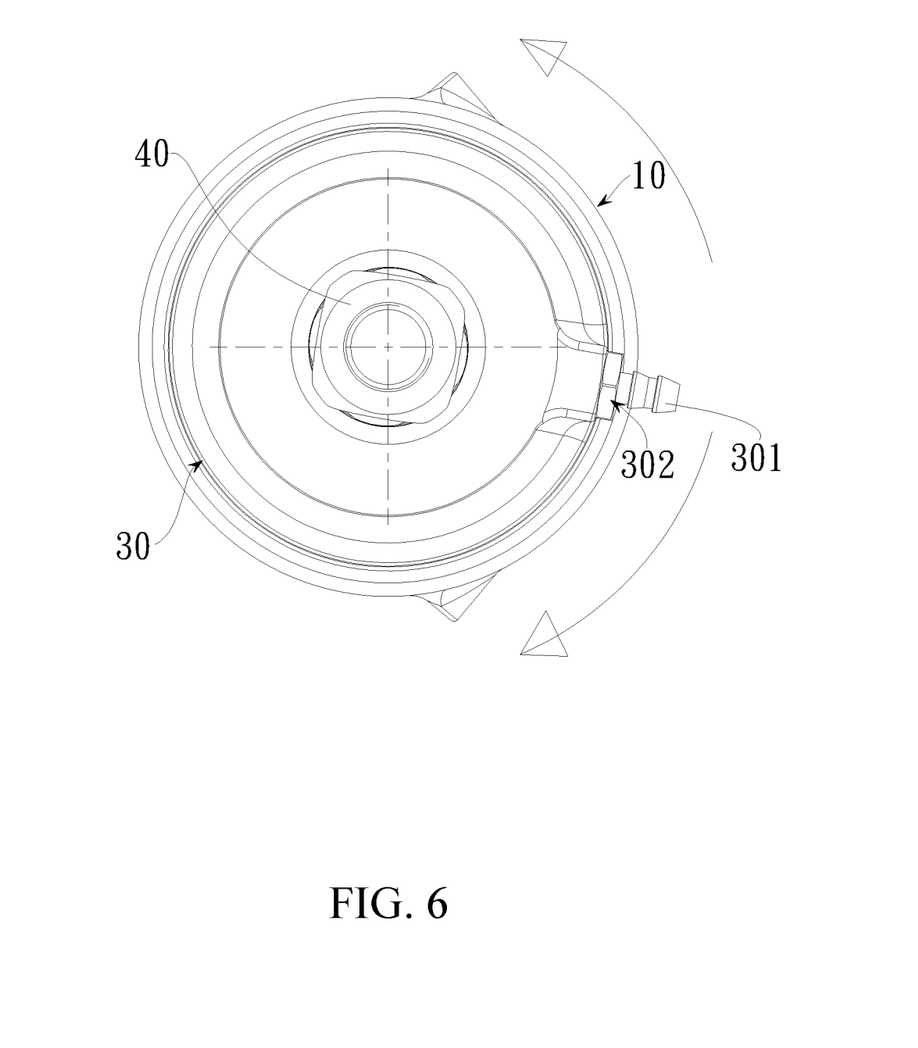
FIG. 6 is a top-view diagram showing a shock and torsion absorber according to another embodiment of the present invention.
Figure 7:
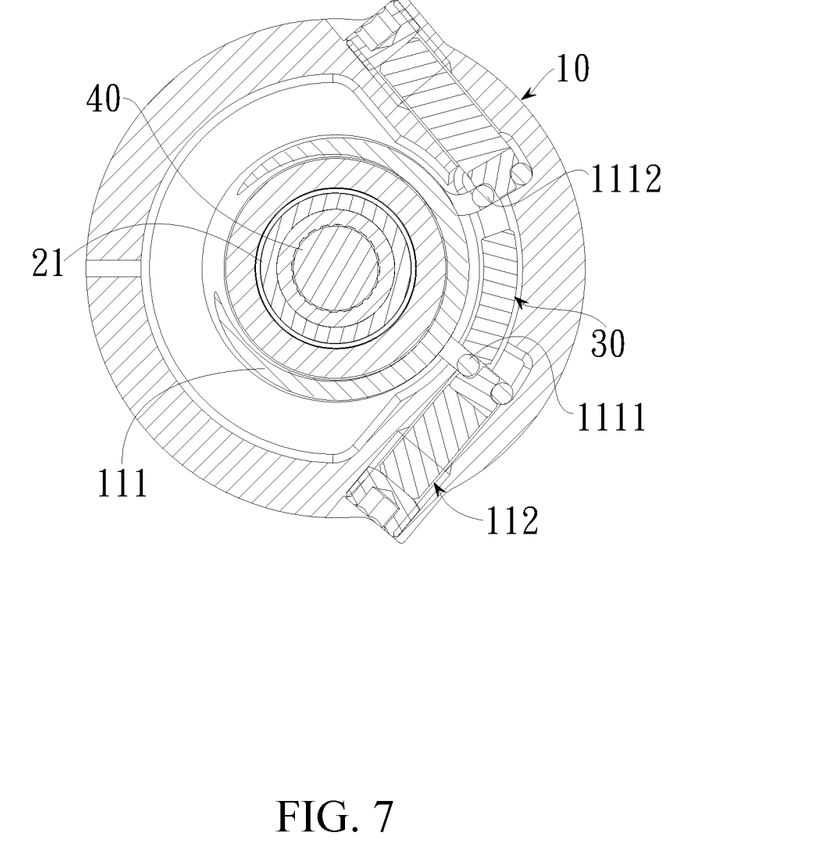
FIG. 7 is a cross-sectional diagram of the shock and torsion absorber of FIG. 6.

As shown in FIGS. 6 and 7, a shock and torsion absorber according to a second embodiment of the present invention has a ring-shaped torsion spring 111. Together with the strength adjustment screws 112, the swivel angle of the joint member 30 is as such limited. The rest of the second embodiment is identical to the previous first embodiment, and the details are omitted.

As described above, the shock and torsion absorber has upper vacuum chamber 50 and lower vacuum chamber 60 formed by the base member 10 and joint member 30. Through the one-way flow design on the seal element 22 and piston 32, air F enters single-directionally into the upper vacuum chamber 50 and lower vacuum chamber 60, so that vacuum and exhaust is achieved. Further, through the mutual contact between the torsion springs 111 and strength adjustment screws 112 within the accommodation space 11, rotational angle between the joint member 30 and base member 10 may be adjusted.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A shock and torsion absorber, comprising:
   a base member having an accommodation space and an exhaust opening;
   a cushion member joined to a bottom end of the base member comprising a casing, a shaft limit element, an elastic element, and an adjustment element, where the shaft limit element and the elastic element are sequentially received in the casing, and a bottom end of the casing is sealed by the adjustment element;
   a limit member comprising a tubular positioning element and a seal element, where a bottom end of the positioning element is threaded through the base member and coupled to the cushion member, and the seal element is joined to a top end of the positioning element;
   a joint member comprising an intake element, a trough, and an axial channel, where the intake element is joined to an outer circumference of the joint member to draw air inside the joint member, the trough is around an inner circumference of the joint member, a piston is tightly housed in the joint member through the trough, a shaft runs through the axial channel and the positioning element, and joins to the shaft limit element for buffering pressure exerted on the joint member
   wherein an upper vacuum chamber is formed inside the joint member above the seal element, and a lower vacuum chamber is formed inside the joint member between the piston and the seal element; when the joint member moves upward, the intake element draws air into the upper vacuum chamber and air in the lower vacuum chamber is expelled through the exhaust opening; and, when the joint member moves downward, air in the upper vacuum chamber flows to the lower vacuum chamber.

2. The shock and torsion absorber according to claim 1, wherein, within the accommodation space, there are two torsion springs and two strength adjustment screws; the torsion springs run through the accommodation space; each torsion spring has a first end and a second end; a plurality of pins are extended from a top side of the piston; the pins fix the joint member so as to adjust the strength adjustment screws' elasticity against the first ends and second ends, and further to limit the joint member's rotational range.

3. The shock and torsion absorber according to claim 1, wherein an intake 1-way valve is configured inside the intake element so that air in the upper vacuum chamber is prevented from backflow through the intake element.

4. The shock and torsion absorber according to claim 1, wherein a seal element 1-way valve is configured in the seal element besides the axial channel so that air drawn through the intake element into the upper vacuum chamber enters single-directionally the lower vacuum chamber.

5. The shock and torsion absorber according to claim 1, wherein a piston 1-way valve is configured in the piston besides the axial channel so that air in the lower vacuum chamber passes single-directionally through the exhaust opening.

6. The shock and torsion absorber according to claim 1, wherein the joint member has a rotational range that is 15 degrees both clockwise and counterclockwise.

\* \* \* \* \*